US012773378B2

(12) United States Patent
Jeanne-Rose et al.

(10) Patent No.: US 12,773,378 B2
(45) Date of Patent: *Oct. 27, 2026

(54) METHOD FOR THE COSMETIC TREATMENT OF KERATIN FIBRES COMPRISING A STAGE OF APPLICATION OF A RARE EARTH METAL COMPOSITION AND A STAGE OF APPLICATION OF A COMPOSITION COMPRISING SURFACTANTS

(71) Applicant: L'OREAL, Paris (FR)

(72) Inventors: Valérie Jeanne-Rose, Aulnay-sous-Bois (FR); Laurent Sabatie, Aulnay-sous-Bois (FR); Henri Samain, Chevilly-Larue (FR)

(73) Assignee: L'OREAL, Paris (FR)

( * ) Notice: Subject to any disclaimer, the term of this patent is extended or adjusted under 35 U.S.C. 154(b) by 992 days.

This patent is subject to a terminal disclaimer.

(21) Appl. No.: 17/787,238

(22) PCT Filed: Dec. 17, 2020

(86) PCT No.: PCT/EP2020/086693

§ 371 (c)(1),
(2) Date: Jun. 17, 2022

(87) PCT Pub. No.: WO2021/122935

PCT Pub. Date: Jun. 24, 2021

(65) Prior Publication Data

US 2023/0025265 A1 Jan. 26, 2023

(30) Foreign Application Priority Data

Dec. 20, 2019 (FR) ...................................... 1915309

(51) Int. Cl.

| | |
|---|---|
| ***A61K 8/19*** | (2006.01) |
| ***A45D 7/06*** | (2006.01) |
| ***A61Q 5/02*** | (2006.01) |
| ***A61Q 5/04*** | (2006.01) |

(52) U.S. Cl.

CPC .................. *A61K 8/19* (2013.01); *A45D 7/06* (2013.01); *A61Q 5/02* (2013.01); *A61Q 5/04* (2013.01); *A61K 2800/884* (2013.01)

(58) Field of Classification Search

CPC ...... A61K 8/19; A61K 2800/884; A61Q 5/02; A61Q 5/04; A45D 7/06

See application file for complete search history.

(56) References Cited

U.S. PATENT DOCUMENTS

| | | | | |
|---|---|---|---|---|
| 4,841,997 | A | 6/1989 | Petrow | |
| 5,112,360 | A * | 5/1992 | Garoche | A61Q 5/10 8/405 |
| 2006/0013780 | A1 * | 1/2006 | Ford | A61Q 19/10 424/70.13 |
| 2012/0060303 | A1 * | 3/2012 | Blackburn | A61K 36/73 8/408 |
| 2018/0338894 | A1 * | 11/2018 | Nöcker | A61K 8/19 |
| 2019/0070083 | A1 | 3/2019 | Krohn et al. | |
| 2019/0070084 | A1 | 3/2019 | Schulze zur Wiesche et al. | |

FOREIGN PATENT DOCUMENTS

| | | | |
|---|---|---|---|
| EP | 0348280 | A1 | 12/1989 |
| FR | 2937539 | A1 | 4/2010 |

OTHER PUBLICATIONS

ChemViews, "Shampoo Science", ChemViews, Jan. 8, 2013. (Year: 2013).*

International Search Report and Written Opinion mailed Feb. 8, 2021, issued in corresponding International Application No. PCT/EP2020/086693, filed Dec. 17, 2020, 12 pages.

* cited by examiner

*Primary Examiner* — Jianfeng Song

(74) *Attorney, Agent, or Firm* — CHRISTENSEN O'CONNOR JOHNSON KINDNESS PLLC

(57) ABSTRACT

The invention relates to a method for the cosmetic treatment of keratin fibres, in particular human keratin fibres, such as the hair, comprising a stage of application of a composition comprising at least one metal compound, the metal of which belongs to the group of the rare earth metals, and then a stage of application of a shampoo comprising at least one surfactant.

13 Claims, No Drawings

METHOD FOR THE COSMETIC TREATMENT OF KERATIN FIBRES COMPRISING A STAGE OF APPLICATION OF A RARE EARTH METAL COMPOSITION AND A STAGE OF APPLICATION OF A COMPOSITION COMPRISING SURFACTANTS

The invention relates to a method for the cosmetic treatment of keratin fibres, in particular human keratin fibres, such as the hair, comprising a stage of application of a composition comprising at least one metal compound, the metal of which belongs to the group of the rare earth metals, and then a stage of application of a shampoo comprising at least one surfactant.

Consumers generally resort to professionals, in particular hairdressers, in order to produce their hairstyle. This hairstyle exhibits a limited lifetime. This is because the hairstyle will be erased when the consumer washes her hair. In the same way, the hairstyle can be destroyed by wearing a helmet or a scarf, or also by wind or rain.

Consumers generally labour to reproduce alone the hairstyle produced by the hairdresser and are thus disappointed by the aesthetic rendering. It is possible to return to the hairdresser in order for the hairstyle to be produced again. Nevertheless, this solution would be very expensive and very time-consuming, and it is thus not realistic.

There thus exists a real need to develop methods for the cosmetic treatment of keratin fibres, in particular human keratin fibres, such as the hair, which make it possible to combine washing and styling with a lasting volumizing effect and which make it possible to reproduce a hairstyle as produced by a hairdresser, without specific expertise.

It has been discovered, surprisingly, that a two-step cosmetic treatment method comprising a stage of application of a composition comprising at least one metal compound, the metal of which belongs to the group of the rare earth metals, followed by a stage of application of a shampoo comprising at least one surfactant, makes it possible to achieve the above objectives, in particular in terms of reproducibility of the hairstyle, of persistence of the volumizing effect after washing, and also of possibility of defining a form one day, and succeeding in reproducing it after shampooing and the following days. The method of the invention makes possible in particular help in the styling/form retention of the hairstyle from one day to the next and between two shampoos.

A subject-matter of the invention is thus a method for the cosmetic treatment of keratin fibres, in particular human keratin fibres, such as the hair, comprising:

i) a stage of application, to a part of the said keratin fibres intended to be shaped, of a composition comprising one or more metal compounds, the metal of which belongs to the group of the rare earth metals, followed by ii) a stage of application, to the keratin fibres, of a shampoo comprising one or more surfactants.

The process according to the invention makes it possible to combine washing and styling with a lasting volumizing effect making it possible to reproduce a hairstyle as produced by a hairdresser, without returning to the hairdresser's salon. The volumizing effect can in addition be adjusted according to the quality and the length of the keratin fibres and the effect desired. Furthermore, the styling can be carried out by a simple move of the hand.

The method according to the invention additionally makes it possible, if desired, to separate the pretreatment stage i) and the washing stage ii) in time.

The method according to the invention can additionally employ, before stage i) or between stages i) and ii), a stage of shaping and/or of styling the keratin fibres.

The method according to the invention can additionally employ, subsequent to stage ii), one or more stages iii) of treatment of the keratin fibres, spread out over time, making it possible to regain the initial shaping of the fibres treated in stage i).

The present invention also relates to a multicompartment kit for the treatment of keratin fibres, in particular human keratin fibres, such as the hair, comprising a first compartment containing a composition comprising one or more metal compounds, the metal of which belongs to the group of the rare earth metals, as defined below, and a second compartment containing a shampoo comprising one or more surfactants as defined below.

Other subject-matters, characteristics, aspects and advantages of the invention will become even more clearly apparent on reading the description and the examples which follow.

In that which follows, and unless otherwise indicated, the limits of a range of values are included in this range, in particular in the expressions "of between" and "ranging from . . . to . . . ".

Moreover, the expression "at least one" used in the present description is equivalent to the expression "one or more".

Composition Applied in Stage i)

The method according to the present invention comprises a stage i) consisting in applying, to keratin fibres, in particular human keratin fibres, such as the hair, a composition comprising one or more metal compounds, the metal of which belongs to the group of the rare earth metals.

Mention may be made, by way of example of a metal belonging to the group of the rare earth metals M, of scandium, yttrium, lanthanum, cerium, praseodymium, neodymium, promethium, samarium, europium, gadolinum, terbium, dysprosium, holmium, erbium, thulium, ytterbium and lutetium.

Preferably, the metal(s) belonging to the group of the rare earth metals are chosen from cerium, yttrium, ytterbium, lanthanum or europium.

According to a specific embodiment, the metal belonging to the group of the rare earth metals is in +III form.

According to the invention, the compound of a metal belonging to the group of the rare earth metals is chosen from salts of rare earth metals, complexes of rare earth metals or oxides of rare earth metals.

The salts of rare earth metals according to the invention can be soluble or insoluble in the composition containing them.

In the case of the salts and complexes of a rare earth metal according to the invention, the compound of a metal belonging to the group of the rare earth metals is in the +III oxidation state.

The metal M can then be combined, via its electron shell, with n1 anionic groups forming an ionic bond with M and/or with n2 groups forming a coordination bond with M. The groups forming a coordination bond are groups having a donor pair, such as carbonyl or amine, for example.

If $n2=0$, the compound of a metal belonging to the group of the rare earth metals forms a salt and, in this case, the metal M is combined with 3 anionic groups.

If $n2>0$, the compound of a metal belonging to the group of the rare earth metals forms a complex and, in this case, the number of anionic groups n1 can vary from 0 to 3.

The metal M is combined with one or more anionic groups and/or one or more groups forming a coordination bond.

Subsequently, the term "ligand" is understood to mean an ion or a molecule carrying a group which is combined, via an ionic bond or a coordination bond, with the metal M. One and the same ligand can carry several groups.

The term "rare earth metal compound" is understood to mean the combination of the metal M with its ligand(s).

A definition of the salts or complexes of rare earth metals can be found in the document: *Progress in the Science and Technology of the Rare Earths*, Volume 1, edited by Leroy Eyring in 1964, published by Macmillan Company and written by F. Gaume-Mahn, page 259 et seq.

The ligands combined with the rare earth metals M to form a salt or a complex and corresponding rare earth metal compounds are described below.

a) Typically, the ligand can be a monoatomic or non-monoatomic monoanionic ion, such as a nitrate or a hydroxide ($OH^-$) or a halide (typically chloride or bromide). By way of example, the rare earth metal compound which results therefrom can then be $MCl_3$, $M(OH)_3$, $M(NO_3)_3$ and the like, and in particular $CeNO_3$, $YNO_3$, $LaNO_3$, $CeCl_3$, $YCl_3$ or $LaCl_3$.

b) the ligand can be a di- or trianionic ion, such as phosphate or sulfate. Mention may be made, by way of example, of the rare earth metal compounds such as $MPO_4$ or $M_2(SO_4)_3$ and in particular $CePO_4$, $YPO_4$, $LaPO_4$, $Ce_2(SO_4)_3$, $Y_2(SO_4)_3$ or $La_2(SO_4)_3$.

c) The ligand can contain one or more groups forming a coordination bond and a functional group forming an ionic bond.

Thus, the ligand can be a mono- or polycarboxylate molecule, such as acetate or succinate. In this case, it is considered that the carboxylate functional group acts as anionic group, via the hydroxyl of the carboxyl group, and acts as group forming a coordination bond, via the doublet of the oxygen of the carbonyl functional group. Thus, the resulting rare earth metal compound can be $M(R—(COO)_n)_{3/n}$. The ligand can, in addition to carrying one or more carboxylates, comprise other functional groups, such as hydroxyls or amines. Thus, the ligand can be to use hydroxycarboxylic acids or aminocarboxylic acids. Mention may be made, as mono- or polycarboxylic compound carrying additional functional groups, of tartrate, citrate, glycolate or ethylenediaminetetraacetate (EDTA) ions.

The ligand can carry a non-localized anionic charge, such as, for example, acetylacetonate. The rare earth metal compounds will then be $M(acetylacetonate)_3$ or $M(acetylacetonate)_3.7H_2O$ where each acetonate is bonded to the metal M by its two carbonyl functional groups, one acting as anionic group and the other as group which is bonded by coordination.

It can also be of the aromatic type, such as a phenol, a cyclopentadiene (*Progress in the Science and Technology of the Rare Earths*, edited by Leroy Eyring and written by F. Gaume-Mahn, page 296) or a pyridine.

The rare earth metal compound can comprise one or more ligands forming a coordination bond and one or more ligands forming an ionic bond. Thus, the rare earth metal compound can be yttrium dihydroxyacetate $Y((OH)_2acetate)$ (*Synthesis and Properties of Yttrium Hydroxyacetate Sols* by S. S. Balabanov, E. M. Gavrishchuk and D. A. Permin, published in the review *Inorganic Materials,* 2012, Vol. 48, No. 5, pp. 500-503, in 2012).

The rare earth metal compound can be a double salt, for example with a rare earth metal M and another cation different from the rare earth metals, such as, for example, an alkali metal $(Li,Ce(SO_4)_2)$ or an alkaline earth metal or an organic catatonic entity, such as a quaternary amine, such as an alkylpyridinium group.

Often very hygroscopic, these rare earth metal compounds can be found in the form of hydrates, such as, for example, $CeCl_3·7H_2O$, $YCl_3·6H_2O$, $LaCl_3·7H_2O$ or $Ce(acetonate)_3·xH_2O$.

Oxides of rare earth metals are known from the state of the art.

In the case of the oxides of rare earth metals according to the invention, the compound of a metal belonging to the group of the rare earth metals is in the +IV oxidation state in the specific case of cerium oxides and in the +III oxidation state for the other rare earth metals as defined above.

Mention may be made, by way of oxide, of the oxides of cerium ($CeO_2$), of lanthanum ($La_2O_3$), of yttrium ($Y_2O_3$), of erbium ($Er_2O_3$), of scandium ($Sc_2O_3$), of ytterbium ($Yb_2O_3$) or of europium ($Eu_2O_3$), preferably the oxides of cerium and of lanthanum. Preferably, the oxides of rare earth metals of use are cerium oxide, lanthanum oxide and yttrium oxide.

Advantageously, the metal(s) belonging to the group of the rare earth metals applied in stage i) are present in a total content ranging from 0.05% to 25% by weight, preferably from 0.5% to 15% by weight, with respect to the total weight of the composition.

The composition applied in stage i) can additionally comprise one or more surfactants chosen from anionic, non-ionic, amphoteric or zwitterionic surfactants and their mixtures.

The surfactants which can be used in the composition applied in stage i) are described below in the shampoo applied in stage ii).

When the composition applied in stage i) comprises one or more surfactants, their total content preferably ranges from 0.5% to 40%, preferably from 1% to 30%.

Preferably, the composition applied in stage i) exhibits an acidic pH, more preferentially of less than or equal to 7, better still of less than or equal to 5.5, and of greater than 3.

Composition Applied in Stage ii)

The method according to the present invention subsequently comprises a stage ii) consisting in applying, to keratin fibres, in particular human keratin fibres, such as the hair, a shampoo comprising one or more surfactants.

The surfactant(s) included in the shampoo can be chosen from cationic, anionic, non-ionic, amphoteric or zwitterionic surfactants, and their mixtures.

Anionic Surfactants

Anionic surfactant is understood to mean a surfactant comprising, as ionic or ionizable groups, only anionic groups.

In the present description, an entity is described as being "anionic" when it possesses at least one permanent negative charge or when it can be ionized to give a negatively charged entity, under the conditions of use of the composition of the invention (medium or pH, for example) and not comprising a cationic charge.

The anionic surfactants can be chosen from sulfate, sulfonate and/or carboxylic (or carboxylate) surfactants. Very obviously, a mixture of these surfactants can be employed.

It is understood, in the present description, that:

the carboxylate anionic surfactants comprise at least one carboxyl or carboxylate (—COOH or —$COO^-$) functional group and can optionally additionally comprise one or more sulfate and/or sulfonate functional groups;

the sulfonate anionic surfactants comprise at least one sulfonate (—$SO_3H$ or —$SO_3^-$) functional group and can optionally additionally comprise one or more sulfate functional groups, but do not comprise a carboxylate functional group; and the sulfate anionic surfactants comprise at least one sulfate functional group but do not comprise a carboxylate or sulfonate functional group.

The carboxylate anionic surfactants capable of being used thus comprise at least one carboxyl or carboxylate (—COOH or —$COO^-$) functional group.

They can be chosen from the following compounds: fatty acids, acylglycinates, acyllactylates, acylsarcosinates, acylglutamates; alkyl-D-galactosideuronic acids, alkyl ether carboxylic acids, alkyl($C_6$-$C_{30}$ aryl) ether carboxylic acids, alkylamido ether carboxylic acids; and also the salts of these compounds; and their mixtures;

the alkyl and/or acyl groups of these compounds comprise from 6 to 30 carbon atoms, in particular from 12 to 28, better still from 14 to 24, indeed even from 16 to 22, carbon atoms; the aryl group preferably denoting a phenyl or benzyl group;

it being possible for these compounds to be polyoxyalkylenated, in particular polyoxyethylenated, and then preferably comprising from 1 to 50 ethylene oxide units, better still from 2 to 10 ethylene oxide units.

Use may also be made of $C_6$-$C_{24}$ alkyl monoesters of polyglycoside-polycarboxylic acids, such as $C_6$-$C_{24}$ alkyl polyglycoside-citrates, $C_6$-$C_{24}$ alkyl polyglycoside-tartrates and $C_6$-$C_{24}$ alkyl polyglycoside-sulfosuccinates, and their salts.

Preferentially, the carboxylate anionic surfactants are chosen from, alone or as a mixture:

fatty acids;

acylglutamates, in particular $C_6$-$C_{24}$, indeed even $C_{12}$-$C_{20}$, acylglutamates, such as stearoylglutamates, and especially disodium stearoylglutamate;

acylsarcosinates, in particular $C_6$-$C_{24}$, indeed even $C_{12}$-$C_{20}$, acylsarcosinates, such as palmitoylsarcosinates, and especially sodium palmitoylsarcosinate;

acyllactylates, in particular $C_{12}$-$C_{28}$, indeed even $C_{14}$-$C_{24}$, acyllactylates, such as behenoyllactylates, and especially sodium behenoyllactylate;

$C_6$-$C_{24}$, in particular $C_{12}$-$C_{20}$, acylglycinates;

($C_6$-$C_{24}$)alkyl ether carboxylates, and in particular ($C_{12}$-$C_{20}$)alkyl ether carboxylates;

polyoxyalkylenated ($C_6$-$C_{24}$)alkyl(amido) ether carboxylic acids, in particular those comprising from 2 to 50 ethylene oxide groups;

in particular in the form of alkali metal, alkaline earth metal, ammonium or amino alcohol salts.

Mention may very particularly be made, among the above carboxylic surfactants, of surfactants of fatty acid type, in particular $C_6$-$C_{30}$ fatty acid type. These surfactants are preferably chosen from the compounds of following formula (a): R—C(O)—OX (a)

with

X denoting a hydrogen atom, an ammonium ion, an ion resulting from an alkali metal or alkaline earth metal or an ion resulting from an organic amine, preferably a hydrogen atom, and R denoting a saturated or unsaturated and linear or branched alkyl group of 7 to 29 carbon atoms.

R preferably denotes a saturated or unsaturated and linear or branched alkyl group of 7 to 23 carbon atoms, preferably of 11 to 21 carbon atoms.

Mention may be made, among the fatty acids, of lauric acid, palmitic acid, myristic acid, stearic acid, oleic acid or behenic acid.

The fatty acids are advantageously chosen from palmitic acid, myristic acid, stearic acid and their mixtures.

Mention may very particularly be made, among the above carboxylic surfactants, of surfactants of sarcosinate type, in particular chosen from ($C_6$-$C_{30}$)acylsarcosinates of following formula (I):

$$R—C(O)—N(CH_3)—CH_2—C(O)—OX \quad (I)$$

with

X denoting a hydrogen atom, an ammonium ion, an ion resulting from an alkali metal or alkaline earth metal or an ion resulting from an organic amine, preferably a hydrogen atom, and R denoting a linear or branched alkyl group of 6 to 30 carbon atoms.

R preferably denotes a linear or branched alkyl group of 8 to 24 carbon atoms, preferably of 12 to 20 carbon atoms.

Mention may be made, among the ($C_6$-$C_{30}$)acylsarcosinates of formula (I) which can be used in the present composition, of palmitoylsarcosinates, stearoylsarcosinates, myristoylsarcosinates, lauroylsarcosinates and cocoylsarcosinates, in acid form or in salified form.

The anionic surfactant(s) of sarcosinate type are advantageously chosen from sodium lauroylsarcosinate, stearoylsarcosine, myristoylsarcosine and their mixtures, preferably from stearoylsarcosine, myristoylsarcosine and their mixtures.

Mention may also be made, among the carboxylic surfactants above, of polyoxyalkylenated alkyl(amido) ether carboxylic acids and their salts, in particular those comprising from 2 to 50 alkylene oxide groups, in particular ethylene oxide groups, such as the compounds provided by Kao under the Akypo names.

The polyoxyalkylenated alkyl(amido) ether carboxylic acids capable of being used are preferably chosen from those of formula (II):

$$R_1—(OC_2H_4)_n—OCH_2COOA \quad (II)$$

in which:

$R_1$ represents a linear or branched $C_6$-$C_{24}$ alkyl or alkenyl radical, a ($C_8$-$C_9$)alkylphenyl radical or an $R_2CONH—CH_2—CH_2—$ radical with $R_2$ denoting a linear or branched $C_9$-$C_{21}$ alkyl or alkenyl radical;

preferably, $R_1$ is a $C_8$-$C_{20}$, preferably $C_8$-$C_{18}$, alkyl radical and aryl preferably denotes phenyl, n is an integer or decimal number (mean value) varying from 2 to 24, preferably from 2 to 10, A denotes H, ammonium, Na, K, Li, Mg or a monoethanolamine or triethanolamine residue.

Use may also be made of mixtures of compounds of formula (II), in particular of mixtures of compounds having different $R_1$ groups.

The polyoxyalkylenated alkyl(amido) ether carboxylic acids which are particularly preferred are those of formula (II) in which:

$R_1$ denotes a $C_{12}$-$C_{14}$ alkyl, cocoyl, oleyl, nonylphenyl or octylphenyl radical, A denotes a hydrogen or sodium atom, and n varies from 2 to 20, preferably from 2 to 10.

More preferentially still, use is made of compounds of formula (II) in which $R_1$ denotes a $C_{12}$ alkyl radical, A denotes a hydrogen or sodium atom and n varies from 2 to 10.

The sulfonate anionic surfactants capable of being used comprise at least one sulfonate (—$SO_3H$ or —$SO_3^-$) functional group.

They can be chosen from the following compounds: alkylsulfonates, alkylamidesulfonates, alkylarylsulfonates, α-olefinsulfonates, paraffinsulfonates, alkyl sulfosuccinates, alkyl ether sulfosuccinates, alkylamide sulfosuccinates, alkyl sulfoacetates, N-acyl taurates, acyl isethionates; alkyl sulfolaurates; as well as the salts of these compounds;

- the alkyl groups of these compounds comprising from 6 to 30 carbon atoms, in particular from 12 to 28, better still from 14 to 24, indeed even from 16 to 22, carbon atoms; the aryl group preferably denoting a phenyl or benzyl group;
- it being possible for these compounds to be polyoxyalkylenated, in particular polyoxyethylenated, and then preferably comprising from 1 to 50 ethylene oxide units, better still from 2 to 10 ethylene oxide units.

Preferentially, the sulfonate anionic surfactants are chosen from, alone or as a mixture:

- $C_6$-$C_{24}$, in particular $C_{12}$-$C_{20}$, alkyl sulfosuccinates, in particular lauryl sulfosuccinates;
- $C_6$-$C_{24}$, in particular $C_{12}$-$C_{20}$, alkyl ether sulfosuccinates;
- ($C_6$-$C_{24}$)acyl isethionates, preferably ($C_{12}$-$C_{18}$)acyl isethionates;
- in particular in the form of alkali metal, alkaline earth metal, ammonium or amino alcohol salts.

The sulfate anionic surfactants capable of being used comprise at least one sulfate (—$OSO_3H$ or —$OSO_3^-$) functional group.

They can be chosen from the following compounds: alkyl sulfates, alkyl ether sulfates, alkylamido ether sulfates, alkylaryl polyether sulfates, monoglyceride sulfates; as well as the salts of these compounds;

- the alkyl groups of these compounds comprising from 6 to 30 carbon atoms, in particular from 12 to 28, better still from 14 to 24, indeed even from 16 to 22, carbon atoms; the aryl group preferably denoting a phenyl or benzyl group;
- these compounds being able to be (poly)oxyalkylenated, in particular (poly)oxyethylenated, and then preferably comprising from 1 to 50 ethylene oxide units, better still from 1 to 10 ethylene oxide units.

Preferentially, the sulfate anionic surfactants are chosen from, alone or as a mixture:

- alkyl sulfates, in particular $C_6$-$C_{24}$, indeed even $C_{12}$-$C_{20}$, alkyl sulfates;
- alkyl ether sulfates, in particular $C_6$-$C_{24}$, indeed even $C_{12}$-$C_{20}$, alkyl ether sulfates, preferably comprising from 1 to 20 ethylene oxide units;
- in particular in the form of alkali metal, alkaline earth metal, ammonium or amino alcohol salts.

When the anionic surfactant is in the salt form, the said salt can be chosen from alkali metal salts, such as the sodium or potassium salt, ammonium salts, amine salts and in particular amino alcohol salts, and alkaline earth metal salts, such as the magnesium salt.

Mention may be made, as examples of amino alcohol salts, of mono-, di- and triethanolamine salts, mono-, di- or triisopropanolamine salts, 2-amino-2-methyl-1-propanol salts, 2-amino-2-methyl-1,3-propanediol salts and tris(hydroxymethyl)aminomethane salts.

The alkali metal or alkaline earth metal salts and in particular the sodium or magnesium salts are preferably used.

Preferentially, the anionic surfactant(s) are chosen from:

- $C_6$-$C_{30}$, in particular $C_8$-$C_{24}$, fatty acids;
- $C_6$-$C_{24}$, in particular $C_{12}$-$C_{20}$, alkyl sulfates;
- $C_6$-$C_{24}$, in particular $C_{12}$-$C_{20}$, alkyl ether sulfates; preferably comprising from 1 to 20 ethylene oxide units;
- $C_6$-$C_{24}$, in particular $C_{12}$-$C_{20}$, alkyl sulfosuccinates; in particular lauryl sulfosuccinates;
- $C_6$-$C_{24}$, in particular $C_{12}$-$C_{20}$, alkyl ether sulfosuccinates;
- ($C_6$-$C_{24}$)acyl isethionates, preferably ($C_{12}$-$C_{18}$)acyl isethionates;
- $C_6$-$C_{24}$, in particular $C_{12}$-$C_{20}$, acylsarcosinates; in particular palmitoylsarcosinates, stearoylsarcosinates or myristoylsarcosinates;
- ($C_6$-$C_{24}$)alkyl ether carboxylates, preferably ($C_{12}$-$C_{20}$) alkyl ether carboxylates;
- polyoxyalkylenated ($C_6$-$C_{24}$)alkyl(amido) ether carboxylic acids and their salts, in particular those comprising from 2 to 50 alkylene oxide groups, in particular ethylene oxide groups;
- $C_6$-$C_{24}$, in particular $C_{12}$-$C_{20}$, acylglutamates;
- $C_6$-$C_{24}$, in particular $C_{12}$-$C_{20}$, acylglycinates;
- and also their salts, in particular their alkali metal or alkaline earth metal or zinc, ammonium or amino alcohol salts;
- and their mixtures.

Advantageously, the anionic surfactant(s) are chosen from carboxylate anionic surfactants and their mixtures.

The anionic surfactant(s) are preferably chosen from $C_6$-$C_{30}$ fatty acids, ($C_6$-$C_{30}$)acylglycinates, ($C_6$-$C_{30}$)acyllactylates, ($C_6$-$C_{30}$)acyl sarcosinates, ($C_6$-$C_{30}$)acylglutamates; alkyl-D-galactosideuronic acids, alkyl ether carboxylic acids, alkyl($C_6$-$C_{30}$ aryl) ether carboxylic acids, alkylamido ether carboxylic acids; $C_6$-$C_{24}$ alkyl monoesters of polyglycoside-polycarboxylic acids; and also the salts of these compounds; and their mixtures.

The anionic surfactant(s) are advantageously chosen from surfactants based on sulfate or sulfonate functional groups, and in particular alkyl sulfates, alkyl ether sulfates, alkylamido ether sulfates, alkyl sulfosuccinates, alkyl ether sulfosuccinates and acyl isethionates.

Non-Ionic Surfactants

The non-ionic surfactants which can be used are described, for example, in the *Handbook of Surfactants* by M. R. Porter, published by Blackie & Son (Glasgow and London), 1991, pp 116-178.

Mention may be made, as examples of non-ionic surfactants, of the following non-ionic surfactants:

- oxyalkylenated ($C_8$-$C_{24}$)alkylphenols;
- saturated or unsaturated, linear or branched, oxyalkylenated or glycerolated, $C_8$ to $C_{40}$ alcohols, comprising one or two fatty chains;
- saturated or unsaturated, linear or branched, oxyalkylenated $C_8$ to $C_{30}$ fatty acid amides;
- esters of saturated or unsaturated, linear or branched, $C_8$-$C_{30}$ acids and of polyols or of polyethylene glycols;
- esters of saturated or unsaturated, linear or branched, $C_8$ to $C_{30}$ acids and of sorbitol which are preferably oxyethylenated;
- esters of fatty acids and of sucrose;
- ($C_8$-$C_{30}$)alkyl(poly)glucosides, ($C_8$-$C_{30}$)alkenyl(poly) glucosides, which are optionally oxyalkylenated (0 to 10 oxyalkylene units) and comprising from 1 to 15 glucose units, ($C_8$-$C_{30}$)alkyl(poly)glucoside esters;
- saturated or unsaturated oxyethylenated vegetable oils;
- condensates of ethylene oxide and/or of propylene oxide;
- N—($C_8$-$C_{30}$)alkylglucamine and N—($C_8$-$C_{30}$)acylmethylglucamine derivatives;

- aldobionamides;
- amine oxides;
- oxyethylenated and/or oxypropylenated silicones;
- and their mixtures.

The oxyalkylene units are more particularly oxyethylene or oxypropylene units, or their combination, preferably oxyethylene units.

The number of moles of ethylene oxide and/or of propylene oxide preferably ranges from 1 to 250, more particularly from 2 to 100 and better still from 2 to 50; the number of moles of glycerol ranges in particular from 1 to 50 and better still from 1 to 10.

Advantageously, the non-ionic surfactants according to the invention do not comprise oxypropylene units.

Use is preferably made, as examples of glycerolated non-ionic surfactants, of mono- or polyglycerolated $C_8$ to $C_{40}$ alcohols, comprising from 1 to 50 mol of glycerol, preferably from 1 to 10 mol of glycerol.

Among the glycerolated alcohols, it is more particularly preferred to use the $C_8/C_{10}$ alcohol having 1 mol of glycerol, the $C_{10}/C_{12}$ alcohol having 1 mol of glycerol and the $C_{12}$ alcohol having 1.5 mol of glycerol.

The non-ionic surfactant(s) which can be used in the composition according to the invention are preferentially chosen from:

- oxyethylenated $C_8$ to $C_{40}$ alcohols comprising from 1 to 100 mol of ethylene oxide, preferably from 2 to 50 and more particularly from 2 to 40 mol of ethylene oxide, and comprising one or two fatty chains;
- saturated or unsaturated oxyethylenated vegetable oils comprising from 1 to 100 mol of ethylene oxide, preferably from 2 to 50;
- ($C_8$-$C_{30}$)alkyl(poly)glucosides, which are optionally oxyalkylenated (0 to 10 EO) and comprising 1 to 15 glucose units;
- mono- or polyglycerolated $C_8$ to $C_{40}$ alcohols, comprising from 1 to 50 mol of glycerol, preferably from 1 to 10 mol of glycerol;
- saturated or unsaturated, linear or branched, oxyalkylenated $C_8$ to $C_{30}$ fatty acid amides;
- esters of saturated or unsaturated, linear or branched, $C_8$ to $C_{30}$ acids and of polyols or of polyethylene glycols;
- and their mixtures.

The non-ionic surfactant(s) which can be used are preferably chosen from alkylpolyglucosides.

Amphoteric or Zwitterionic Surfactants

The amphoteric surfactants capable of being used in the invention can be optionally quaternized secondary or tertiary aliphatic amine derivatives, in which the aliphatic group is a linear or branched chain comprising from 8 to 22 carbon atoms, the said amine derivatives containing at least one anionic group, such as, for example, a carboxylate, sulfonate, sulfate, phosphate or phosphonate group.

Mention may in particular be made of ($C_8$-$C_{20}$)alkyl betaines, sulfobetaines, ($C_8$-$C_{20}$)alkyl sulfobetaines, ($C_8$-$C_{20}$)alkylamido ($C_1$-$C_6$)alkyl betaines, such as cocoamidopropyl betaine, ($C_8$-$C_{20}$)alkylamido ($C_1$-$C_6$)alkyl sulfobetaines, as well as their mixtures.

Mention may also be made, among the derivatives of optionally quaternized secondary or tertiary aliphatic amines capable of being employed, of the products with the following respective structures (A1) and (A2):

$$R_a\text{—CON(Z)CH}_2\text{—(CH}_2)_m\text{—N}^+(R_b)(R_c)(\text{CH}_2\text{COO}^-) \quad \text{(A1)}$$

in which:

- $R_a$ represents a $C_{10}$-$C_{30}$ alkyl or alkenyl group derived from an acid $R_a$—COOH preferably present in hydrolysed coconut oil, or a heptyl, nonyl or undecyl group,
- $R_b$ represents a β-hydroxyethyl group,
- $R_c$ represents a carboxymethyl group;
- m is equal to 0, 1 or 2, and
- Z represents a hydrogen atom or a hydroxyethyl or carboxymethyl group;

$$R_{a'}\text{—CON(Z)CH}_2\text{—(CH}_2)_{m'}\text{—N(B)(B')} \quad \text{(A2)}$$

in which:

- B represents —$CH_2CH_2OX'$, with X' representing —$CH_2$—COOH, $CH_2$—COOZ', —$CH_2CH_2$—COOH, —$CH_2CH_2$—COOZ', or a hydrogen atom,
- B' represents —$(CH_2)_z$—Y', with z=1 or 2, and Y' representing —COOH, —COOZ', —$CH_2$—CHOH—$SO_3H$ or $CH_2$—CHOH—$SO_3Z'$,
- m' is equal to 0, 1 or 2,
- Z represents a hydrogen atom or a hydroxyethyl or carboxymethyl group,
- Z' represents an ion resulting from an alkali metal or alkaline earth metal, such as sodium, potassium or magnesium; an ammonium ion; or an ion resulting from an organic amine and in particular from an amino alcohol, such as mono-, di- and triethanolamine, mono-, di- or triisopropanolamine, 2-amino-2-methyl-1-propanol, 2-amino-2-methyl-1,3-propanediol and tris(hydroxymethyl)aminomethane, and
- $R_{a'}$ represents a $C_{10}$-$C_{30}$ alkyl or alkenyl group of an acid $R_{a'}$COOH preferably present in hydrolysed linseed oil or coconut oil, an alkyl group, in particular a $C_{17}$ alkyl group, and its iso form, or an unsaturated $C_{17}$ group.

The compounds corresponding to the formula (A2) are particularly preferred.

Mention may be made, among the compounds of formula (A2) for which X' represents a hydrogen atom, of the compounds known under the (CTFA) names sodium cocoamphoacetate, sodium lauroamphoacetate, sodium caproamphoacetate and sodium capryloamphoacetate.

Other compounds of formula (A2) are known under the (CTFA) names disodium cocoamphodiacetate, disodium lauroamphodiacetate, disodium caproamphodiacetate, disodium capryloamphodiacetate, disodium cocoamphodipropionate, disodium lauroamphodipropionate, disodium caproamphodipropionate, disodium capryloamphodipropionate, lauroamphodipropionic acid and cocoamphodipropionic acid.

Mention may be made, as examples of compounds of formula (A2), of the cocoamphodiacetate sold by Rhodia under the trade name Miranol® C2M Concentrate, the sodium cocoamphoacetate sold under the trade name Miranol Ultra C 32 and the product sold by Chimex under the trade name Chimexane HA.

Use may also be made of the compounds of formula (A3):

$$R_{a''}\text{—NH—CH(Y'')—(CH}_2)_n\text{—C(O)—NH—(CH}_2)_{n'}\text{—N}(R_d)(R_e) \quad \text{(A3)}$$

in which:

- $R_{a''}$ represents a $C_{10}$-$C_{30}$ alkyl or alkenyl group of an acid;
- $R_{a''}$—C(O)OH, preferably present in hydrolysed linseed oil or coconut oil;
- Y" represents the —C(O)OH, —C(O)OZ" or —$CH_2$—CH(OH)—$SO_3H$ group or the $CH_2$—CH(OH)—$SO_3$—Z" group, with Z" representing a cation resulting from an alkali metal or alkaline earth metal, such as sodium, an ammonium ion or an ion resulting from an organic amine;

$R_d$ and $R_e$, independently of each other, represent a $C_1$-$C_4$ alkyl or hydroxyalkyl radical; and n and n', independently of each other, denote an integer ranging from 1 to 3.

Mention may in particular be made, among the compounds of formula (A3), of the compound classified in the CTFA dictionary under the name sodium diethylaminopropyl cocoaspartamide and in particular of that sold by Chimex under the name Chimexane HB.

The amphoteric surfactant(s) are advantageously chosen from ($C_8$-$C_{20}$)alkyl betaines and ($C_8$-$C_{20}$)alkylamido ($C_1$-$C_6$)alkyl betaines.

Advantageously, the surfactant(s) applied in stage ii) are present in a total content ranging from 1% to 40% by weight, preferably from 2% to 20% by weight, with respect to the total weight of the composition.

The compositions applied in stages i) and ii) according to the present invention can optionally additionally comprise one or more additives, other than the compounds of the invention, among which mention may be made of cationic, non-ionic, amphoteric or zwitterionic surfactants, and their mixtures, cationic, anionic, non-ionic or amphoteric polymers, or their mixtures, antidandruff agents, anti-seborrhoeic agents, vitamins and provitamins, including panthenol, sunscreens, sequestering agents, plasticizers, solubilizing agents, acidifying agents, alkaline agents, inorganic or organic thickening agents, in particular polymeric thickening agents, antioxidants, hydroxy acids, fragrances and preservatives.

Of course, a person skilled in the art will take care to choose this or these optional additional compounds so that the advantageous properties intrinsically associated with the composition according to the invention are not, or not substantially, detrimentally affected by the envisaged addition(s).

The above additives can generally be present in an amount of, for each of them, between 0% and 20% by weight, with respect to the total weight of the composition.

Implementation of the Method

The method according to the invention employs:

i) a stage of application, to a part of the keratin fibres intended to be shaped, of a composition comprising one or more metal compounds, the metal of which belongs to the group of the rare earth metals, as defined above, followed by ii) a stage of application, to the keratin fibres, of a shampoo comprising one or more surfactants, as defined above.

Stages i) and ii) can be carried out immediately following one another or be separated in time.

Advantageously, the composition applied in stage i) is applied to the parts of the keratin fibres to which it is desired to give contours, i.e. at the place(s) where it is desired for the styling effect to operate.

Preferably, the composition applied in stage ii) is applied to all of the keratin fibres.

Stage i) can be carried out on dry or wet keratin fibres.

In the case where the composition applied in stage i) does not comprise surfactants, the method according to the invention takes the form of a treatment comprising a pretreatment stage i), followed by a stage ii) of washing with a shampoo composition.

In the case where the composition applied in stage i) additionally comprises one or more surfactants, the method according to the invention takes the form of a treatment comprising two stages i) and ii) of washing with two different shampoo compositions.

Preferably, the method according to the invention employs, before stage i) or between stages i) and ii), a stage of shaping the keratin fibres.

Preferably, the shaping of the keratin fibres is carried out by means of a brush, of a hairdryer, of heating tongs (160-230° C.), of hairsetting rollers or more simply with the hands.

Preferably, stage ii) is followed by one or more stages iii) of treatment of the fibres, spaced out in time, making it possible to regain the initial shaping of the fibres treated by the composition of stage i); preferably, this stage of treatment of the keratin fibres consists in brushing the said fibres or in drying the said fibres.

Preferably, a shampooing is carried out between two stages iii) spaced out in time.

Preferably, stage i) is preceded by a stage of shaping and/or of styling the keratin fibres.

In a preferred embodiment of the method of the invention, contours are imposed on certain locks of the head of hair, the remainder of the head of hair retaining its natural contours.

The locks on which contours have been imposed are subsequently treated with a composition comprising one or more metal compounds as described above (stage i)).

A variable amount of composition of metal compound(s) is applied according to the volumizing effect desired, that is to say according to the strength of the contours imprinted on each lock.

The head of hair is subsequently washed with a shampoo comprising one or more surfactants as described above (stage ii)). The effect of this washing stage is to destroy the hairstyle under the effect of the water.

The head of hair is subsequently dried with a hairdryer, without bothering about the hairstyle, and then brushed. The locks not treated with the composition of metal compound(s) regain their natural vertical position. The locks treated with the composition of metal compound(s) resume the contours applied prior to stage i), the locks which have been treated with the greatest amount of composition of metal compound (s) exhibiting the greatest volumizing effect. The initial hairstyle, produced prior to stage i), is then reproduced.

In a specific alternative of this embodiment, the head of hair is subsequently again washed, for example after several days, with a shampoo comprising one or more surfactants as described above (stage ii)). The initial hairstyle is then reproduced by simple drying and/or styling of the head of hair. In particular, the hairstyle is produced by a rapid method, such as combing and/or brushing and/or passing the fingers through the head of hair.

The present invention also relates to a multicompartment kit for the treatment of keratin fibres, in particular human keratin fibres, such as the hair, comprising a first compartment containing a composition comprising one or more metal compounds, the metal of which belongs to the group of the rare earth metals, as defined above, and a second compartment containing a shampoo comprising one or more surfactants as defined above.

EXAMPLES

In the examples which follow, all the amounts are given, unless otherwise indicated, as percentage by weight of active material (AM), with respect to the total weight of the composition.

Example 1

Compositions A1, A2 and B1 to B3 were prepared from the ingredients, the contents of which are shown as active material in the tables below:

TABLE 1

| Compositions A | | |
|---|---|---|
| Ingredients | A1 | A2 |
| Yttrium hydroxyacetate | 10 | 1 |
| Water | q.s. for 100 | q.s. for 100 |

TABLE 2

| Compositions B | | | |
|---|---|---|---|
| Ingredients | B1 | B2 | B3 |
| Coco glucoside[1] | 5 (AM) | | |
| Coco betaine at 30% in water[2] | — | 5 (AM) | — |
| Sodium laureth sulfate at 70% in water[3] | — | — | 5% (AM) |
| Water | q.s. for 100 | q.s. for 100 | q.s. for 100 |

[1]sold under the name Plantacare 818 UP by BASF
[2]sold under the name Dehyton AB 30 by BASF
[3]sold under the name Texapon AOS 225 UP by BASF For the above example, use is made of a malleable head with a head of hair of Caucasian hairs and a mid-length haircut With this head of hair and hairstyle, the dry hairs overall assume an arrangement such that the hairs follow gravity. Using a brush, a part of the head of hair is shaped, namely the hairs of the sides. This shaping brings the hairs to be orthogonal overall to gravity. At this stage, the shape given is weak and care is taken not to move the head in order to maintain it.

The parts shaped (that is to say, the hairs on the sides) are subsequently treated with the compositions A1 or A2, 3 g of composition being localized, by virtue of a pump-action spray, at the places which it is desired to subsequently style, these being maintained in a position orthogonal to the direction of the natural hairs before styling (direction of gravity).

Without waiting for the drying, the hairs are subsequently washed with the compositions B1, B2 or B3. The compositions are, with the water which is added during the shampooing, distributed over the whole of the head of hair. The whole of the head of hair is then subjected to a final rinsing. During the rinsing, under the effect of gravity and then after disentangling, the hairs assume a position parallel overall to gravity close to the initial position before shaping. The hairs are subsequently dried under the effect of a hairdryer without shaping but while carrying out combing, from the bottom upwards, parallel to gravity. Once dry, the hairs are parallel overall to gravity.

The possibility of restyling the hairs, that is to say of regaining the shaping carried out beforehand, is graded from 0 (very low possibility of shaping) to 10 (strong possibility of shaping).

To do this, the hairs are combed in a way non-parallel to gravity. In order to make sure that the shape is indeed given, a comb is run through the hair, the comb is removed and then the malleable head is rotated by 15° to the right and then 15° to the left. Either the shape given by running the comb through the hair is maintained, or the shape given is lost and the hairs again end up parallel to gravity.

When the shape is maintained after a comb has been run through the hair and the comb has been removed, a grade of 10 is given.

When the shape is lost at the actual time when the comb is removed, even without having to rotate the malleable head, a grade of 0 is given.

When the shape is given but the hairs partially hang down in the direction of gravity, an intermediate grade is given.

The results shown in the table below are mean results for retention of the shape as shown above obtained from the evaluation by several subjects.

TABLE 3

| Compositions | Composition B | | |
|---|---|---|---|
| A | B1 | B2 | B3 |
| A1 | 8 | 9 | 10 |
| A2 | 7 | 7 | 8 |

The method according to the invention in the form of a treatment comprising a stage of pretreatment i) with a composition comprising rare earth metals, followed by a stage of washing ii) with a shampoo, makes it possible to easily reproduce the hairstyle produced beforehand.

An impression of stronger hairs is noted visually, owing to the fact that the head of hair is put into a shape where not all the hairs follow the vertical.

It is also noted that, when the head of hair is touched, the hairs become individual and the shape can be put back into place by the simple effect of the fingers or of running a comb quickly through the hair. These effects, related to the shape, without exhibiting a welding effect, contribute to the impression that the hairs are stronger.

The same test as above is carried out, this time performing three washing operations with the compositions B1, B2 or B3. The results are shown in the table below.

TABLE 4

| Compositions | Composition B | | |
|---|---|---|---|
| A | B1 | B2 | B3 |
| A1 | 7 | 7 | 8 |
| A2 | 5 | 6 | 7 |

This method employed according to the invention is also lasting since it makes it possible to easily reproduce the hairstyle produced beforehand, even after three washing operations.

As above, the same impression exists of stronger hairs. The fact that the possibility of shaping endures after 3 shampooing operations accentuates the impression of having stronger hairs.

Example 2

Compositions A3, A4 and A5 were prepared from ingredients, the contents of which are shown as active material in the tables below:

TABLE 5

| Compositions A | | | |
|---|---|---|---|
| Ingredients | A3 | A4 | A5 |
| Lanthanum chloride heptahydrate | 10% | 10% | — |
| Yttrium hydroxy acetate hexahydrate | — | — | 10% |
| Coco betaine at 30% in water[2] | 5% AM | — | — |

TABLE 5-continued

| Compositions A | | | |
|---|---|---|---|
| Ingredients | A3 | A4 | A5 |
| Sodium laureth sulfate at 70% in water[3] | — | 5% AM | — |
| Coco glucoside[1] | — | — | 5% AM |
| Water | q.s. for 100 | q.s. for 100 | q.s. for 100 |

[1]sold under the name Plantacare 818 UP by BASF
[2]sold under the name Dehyton AB 30 by BASF
[3]sold under the name Texapon AOS 225 UP by BASF A head of hair of Caucasian hairs is prepared as described in Example 1. The parts shaped (thus on the sides) are subsequently treated with the compositions A3 or A4 or A5, 2.5 grams being localized, by hand, at the places which it is subsequently intended to style and the hairs then being massaged so as to produce a foam. The whole of the head of hair is rinsed. The hairs are left and dry in the open air.

The next day, the hairs of the head of hair are washed with the compositions B1, B2 or B3. A final rinsing is then carried out on the whole of the head of hair.

During the rinsing, under the effect of gravity and then after disentangling, the hairs assume a position parallel overall to gravity. The hairs are subsequently dried with a hairdryer without carrying out shaping.

The same evaluation as described in Example 1 is carried out, leading to the following results:

TABLE 6

| Compositions | Composition B | | |
|---|---|---|---|
| A | B1 | B2 | B3 |
| A3 | 8 | 6 | 6 |
| A4 | 8 | 6 | 6 |
| A5 | 7 | 7 | 8 |

The method employed according to the invention in the form of a treatment comprising two successive stages i) and ii) of washing with two different shampoos makes it possible to easily reproduce the hairstyle produced beforehand. It exhibits the advantage of being able to define one day an effect of shaping a head of hair, for example with the help of a specialist, such as a hairdresser, and then, the next day, to put the head of hair into shape in person without particular skill.

The same test as above is carried out, this time performing three washing operations with the compositions B1, B2 or B3 described in Example 1. The results are shown in the table below.

TABLE 7

| Compositions | Composition B | | |
|---|---|---|---|
| A | B1 | B2 | B3 |
| A3 | 7 | 4 | 4 |
| A4 | 8 | 4 | 4 |
| A5 | 7 | 6 | 7 |

This method employed according to the invention is also lasting since it makes it possible to easily reproduce the hairstyle produced beforehand, even after three washing operations.

The invention claimed is:

1. A method for shaping the hair comprising:

i) a stage of application, to a part of the said hair intended to be shaped, of a composition comprising one or more metal compounds, the metal of which is chosen from yttrium, ytterbium, lanthanum and europium, followed by ii) a stage of application, to the hair, of a shampoo comprising one or more surfactants, and wherein a stage of shaping the hair is implemented before stage i) or between stages i) and ii).

2. The method for shaping the hair according to claim 1, wherein the metal of the one or more metal compound is in the +III oxidation state.

3. The method for shaping the hair according to claim 1, wherein the one or more metal compounds are chosen from salts of rare earth metals, complexes of rare earth metals or oxides of rare earth metals; the rare earth metals being chosen from yttrium, ytterbium, lanthanum and europium.

4. The method for shaping the hair according to claim 1, wherein the one or more metal compound are chosen from yttrium dihydroxyacetate, yttrium chloride, lanthanum chloride, lanthanum oxide, yttrium oxide, ytterbium oxide, europium oxide, and mixtures thereof.

5. The method for shaping the hair according to claim 1, wherein the metal compound(s) are present in a content ranging from 0.05% to 25% by weight, with respect to the total weight of the composition.

6. The method for shaping the hair according to claim 1, wherein the composition applied in stage i) exhibits an acidic pH.

7. The method for shaping the hair according to claim 1, wherein the shampoo applied in stage ii) comprises one or more surfactants chosen from anionic, non-ionic, amphoteric or zwitterionic surfactants, and mixtures thereof.

8. The method for shaping the hair according to claim 1, wherein the shampoo applied in stage ii) comprises a total content of surfactants ranging from 1% to 40% by weight, with respect to the total weight of the composition.

9. The method for shaping the hair according to claim 1, wherein the composition applied in stage i) additionally comprises one or more surfactants chosen from anionic, non-ionic, amphoteric or zwitterionic surfactants, and mixtures thereof.

10. The method for shaping the hair according to claim 1, wherein the shaping is carried out by means of a brush, of a hairdryer, of heating tongs, of hairsetting rollers or more simply with the hands.

11. The method for shaping the hair according to claim 1, wherein stage ii) is followed by one or more stages iii) of treatment of the hair, spaced out in time, making it possible to regain the initial shaping of the hair treated by the composition of stage i).

12. The method for shaping the hair according to claim 11, wherein a shampooing is carried out between two stages iii) spaced out in time.

13. The method for shaping the hair according to claim 1, wherein the metal of the one or more metal compounds is yttrium.

* * * * *